US 6,636,770 B2

(12) United States Patent
Ripart

(10) Patent No.: US 6,636,770 B2
(45) Date of Patent: Oct. 21, 2003

(54) SINGLE-PATH LEAD FOR AN ACTIVE IMPLANTABLE MEDICAL DEVICE OF THE IMPLANTABLE DEFIBRILLATOR/ CARDIOVERTOR TYPE

(75) Inventor: Alain Ripart, Gif-sur-Yvette (FR)

(73) Assignee: Ela Medical, Montrouge (FR)

(*) Notice: Subject to any disclaimer, the term of this patent is extended or adjusted under 35 U.S.C. 154(b) by 106 days.

(21) Appl. No.: 09/766,886

(22) Filed: Jan. 19, 2001

(65) Prior Publication Data

US 2001/0025194 A1 Sep. 27, 2001

(30) Foreign Application Priority Data

Jan. 19, 2000 (FR) .............................. 00 00632

(51) Int. Cl.[7] .............................. A61N 1/00; A61N 1/04; A61N 1/05; A61N 1/06
(52) U.S. Cl. ..................................... 607/122
(58) Field of Search ..................... 128/786; 600/508; 607/122, 4, 123, 126

(56) References Cited

U.S. PATENT DOCUMENTS

| | | | |
|---|---|---|---|
| 4,499,907 A | * 2/1985 | Kallok et al. | 128/786 |
| 5,476,499 A | * 12/1995 | Hirschberg | 607/123 |
| 5,713,945 A | * 2/1998 | Fischer et al. | 607/122 |
| 6,007,493 A | * 12/1999 | Ericksen et al. | 600/508 |
| 6,178,350 B1 | * 1/2001 | Olson et al. | 607/4 |
| 6,430,449 B1 | * 8/2002 | Hsu et al. | 607/126 |

FOREIGN PATENT DOCUMENTS

| | | | |
|---|---|---|---|
| DE | 19800697 | * 10/1998 | A61N/1/05 |
| DE | 198 00 697 A1 | 7/1999 | A61N/1/05 |

* cited by examiner

*Primary Examiner*—Henry Bennett
*Assistant Examiner*—Sabrina Dagostino
(74) *Attorney, Agent, or Firm*—Orrick, herrington & Sutcliffe LLP

(57) ABSTRACT

A single-path lead for an active implantable medical device of the implantable defibrillator/cardioverter type. The lead includes a lead body (10) carrying first (14) and second (16) atrial electrodes for sensing an atrial cardiac signal, first (18) and second (20) ventricular electrodes for sensing a ventricular cardiac signal, one (18) of these ventricular electrodes also being an electrode for use in the application of defibrillation or cardioversion energy (shock pulses), and a supra-ventricular electrode (12) for use in the application of the aforementioned shock energy for the defibrillation or cardioversion. An electric connection (24), preferably internal to the lead, joins together one of the atrial electrodes (14; 16) and the supra-ventricular electrode (12), the aforementioned atrial cardiac signal being collected by the lead between, on the one hand, the supra-ventricular electrode (12) and the atrial electrode (14; 16) which is connected to it and, on the second hand, the other atrial electrode (16; 14).

3 Claims, 1 Drawing Sheet

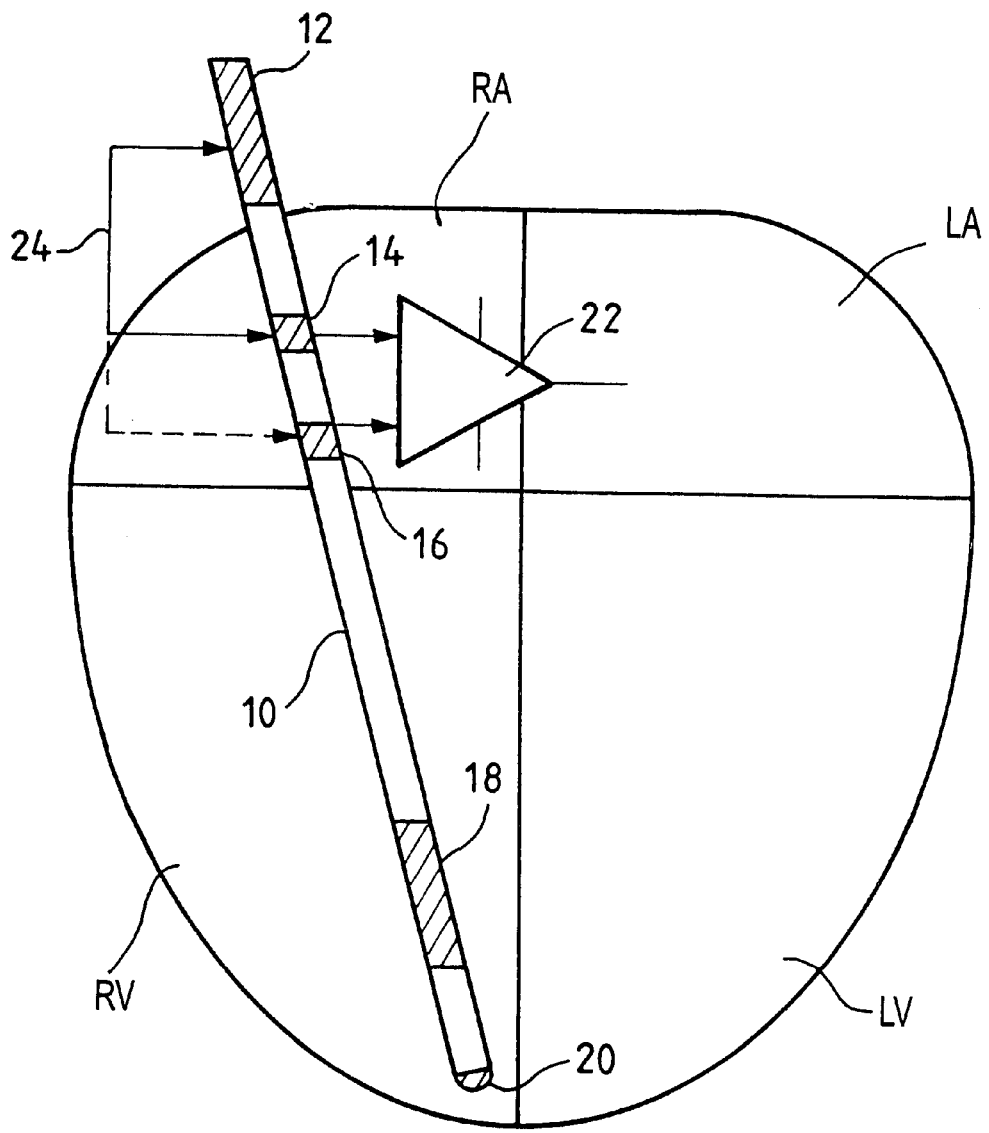
FIG_1

SINGLE-PATH LEAD FOR AN ACTIVE IMPLANTABLE MEDICAL DEVICE OF THE IMPLANTABLE DEFIBRILLATOR/CARDIOVERTOR TYPE

FIELD OF THE INVENTION

The present invention relates to "active implantable medical devices" as such devices are defined by the Jun. 20, 1990 directive 90/385/CEE of the Council of the European Communities, and more particularly the family of the devices which are able to deliver to the heart pulses of high energy (i.e., energy levels significantly exceeding the energy provided for simple stimulation) to try to terminate a tachyarhythmia. These devices are called "implantable defibrillators" or "implantable cardiovertors", it being understood, however, that the invention also covers the so-called implantable defibrillator/cardiovertor/pacemakers, and defibrillator/pacemakers.

BACKGROUND OF THE INVENTION

The known implantable devices typically have two components, namely a pulse generator, and a lead or a system of leads. The pulse generator is responsible for monitoring the cardiac activity and generating pulses of high energy when the heart presents a ventricular arrhythmia that is deemed likely to be susceptible to treatment. When this high energy lies in a range between approximately 0.1 and 10.0 Joules (J), one calls this therapy by the name of "cardioversion" and the electric energy delivered is called a "cardioversion shock". When the high energy is higher than approximately 10 J, the electric energy delivered is then called a "defibrillation shock".

To this generator are connected one or more leads, fitted with electrodes, whose role is to distribute the shock energy to the heart in a suitable manner. European Patent EP-A-0, 773,039 and its corresponding U.S. Pat. No. 5,776,165, both assigned to the assignee hereof, ELA Médical, Montrouge, France, describe such a generator/lead unit with means for selecting an optimal configuration for the application of the cardioversion or defibrillation shock.

BACKGROUND OF THE INVENTION

The present invention, as discussed below, relates to the particular situation where the pulse generator is connected to a lead known as a "mono-body" or "single-path" lead, which is a single lead carrying thereon the various electrodes that are able to deliver the defibrillation and/or cardioversion shock.

The German Patent Application DE-A-198 00 697 (assigned to Biotronik) describes such a single-path lead, including two ventricular electrodes for sensing a cardiac signal, a ventricular electrode for delivery of a shock, an atrial electrode for sensing a cardiac signal, and an atrial electrode for delivery of a shock. The two atrial electrodes (detection and shock) are electrically connected together, which makes it possible to avoid a supplementary (additional) conductor in the lead (i.e., there are four conductors instead of five) and also to avoid an extra connection terminal in the connector head of the defibrillator.

In reality, however the "atrial" shock electrode is an electrode that is positioned mainly in the high vena cava, and so it does not allow for a suitable sensing of a cardiac signal. For this reason, it is envisaged that an atrial detection electrode, placed indeed in the atrium, is able to collect (sense) the electric activity available at this location within the myocardium. But the measurement of the atrial activity is obtained between this atrial detection electrode and a ground reference (i.e., a measurement in a monopolar mode). This leads to a notable degradation of the signal-to-noise ratio, because the lead is a floating lead.

OBJECTS AND SUMMARY OF THE INVENTION

It is, therefore, an object of the present invention to cure this noted disadvantage by proposing a structure of an improved lead which, without increasing the number of conductors or electric terminals at the generator, gives a better quality measurement of the electric activity in the atrium.

To this end, the lead of the present invention is directed to a lead body carrying a first atrial electrode and a second atrial electrode for sensing an atrial cardiac signal, a first ventricular electrode and a second ventricular electrode for sensing a ventricular cardiac signal, one of these ventricular electrodes also being an electrode for the application of defibrillation or cardioversion shock energy, and a supra-ventricular electrode for the application of the aforementioned defibrillation or cardioversion shock energy. An electric connection, preferably internal to said lead, joins together one of the atrial electrodes and the supra-ventricular electrode, the aforementioned atrial cardiac signal thus being collected by the lead between, on the one hand, the ensemble comprising the supra-ventricular electrode and the atrial electrode connected together, and on the other hand, the other atrial electrode.

In a preferred embodiment, the atrial electrode connected to the supra-ventricular electrode is a proximal electrode, and the other atrial electrode is a distal electrode.

BRIEF DESCRIPTION OF THE DRAWING

Further features, characteristics, and advantages of the present invention will appear to a person of ordinary skill in the art in view of the following description, made with reference to the annexed drawing, which is a diagrammatic representation of the cardiac muscle with an implanted single-path lead.

DETAILED DESCRIPTION OF THE INVENTION

With reference to FIG. 1, a cardiac muscle with its four cavities is schematically represented: right atrium RA, right ventricle RV, left atrium LA and left ventricle LV.

A single-path lead 10 is introduced by the venous network into the two atrial and ventricular cavities, so as to detect there the cardiac activity and to apply, as needed, a defibrillation or cardioversion shock. This single path lead 10 comprises, in the direction from proximal to distal extremities:

(1) a first shock electrode 12, constituting, for example, the positive terminal of application of the defibrillation or cardioversion potential; this electrode is an electrode known as "supra-ventricular electrode", typically a coil electrode positioned principally in the high vena cava;

(2) an atrial proximal electrode 14;

(3) an atrial distal electrode 16;

(4) a second shock electrode 18 located in the ventricle, constituting, for example, the negative terminal of application of the defibrillation or cardioversion potential;

and (5) a ventricular electrode at the extremity 20.

In a manner characteristic of the present invention, the atrial activity is detected in a bipolar mode by a differential measurement operated between electrodes 14 and 16. The differential measurement is shown schematically by the use of a conventional operational amplifier 22, as is well known in the art. In addition, lead 10 comprises an internal connection 24, illustrated as extending between supra-ventricular electrode 12 and proximal atrial electrode proximal 14. Connection 24 carries out on the corresponding input of amplifier 22 the sum of the signals present on the two electrodes. However, because of its position external to the atrium, supra-ventricular electrode 12 does not collect (sense) a cardiac signal.

The electrodes 12 and 14 are electrically connected and the signals present at nodes 14 and 16 are applied to the respective inputs of differential amplifier 22. This amplifier must have a very good rejection rate, which allows for the programming of high sensitivity, for example, a sensitivity of 0.15 mV: such a value is necessary to detect the atrial signals sensed from a floating lead. Indeed, it is noted that none of the electrodes is in contact with cardiac tissue.

In an alternative embodiment, instead of providing an internal connection 24, connection 24 can be carried out by a connector of the defibrillator, i.e., a connector external to the lead, but this alternative implies the presence of an additional conductor in the lead.

In another alternative embodiment, the supra-ventricular electrode 12 may be connected to the distal atrial electrode 16 instead of being connected to the proximal atrial electrode 14. This particular configuration is a preferred embodiment because it insures for a better rejection of the common mode by the effect of shielding around the electrode 14.

The ventricular electrodes 18 and 20 also can be used for the sensing of a ventricular signal: the implantable device pulse generator operates thus in a double chamber mode for detection (i.e., detection in the atrium and in the ventricle), with application of the defibrillation and cardioversion shock in the ventricle only, delivered between the ventricular electrode 18 and the supra-ventricular electrode 12.

One skilled in the art will appreciate that the present invention can be practiced by other than the described embodiments, which are presented for the purposes of illustration and not of limitation.

I claim:

1. A single-path lead for an active implantable medical device of the defibrillator/cardiovertor type, having a body comprising:

a first atrial electrode and a second atrial electrode for sensing an atrial cardiac signal;

a first ventricular electrode and a second ventricular electrode for sensing a ventricular cardiac signal, one of said first and second ventricular electrodes further comprising an electrode for applying a defibrillation or cardioversion energy shock;

a supra-ventricular electrode for applying said defibrillation or cardioversion energy shock;

an electric connection between one of said first and second atrial electrodes and the supra-ventricular electrode, said atrial cardiac signal being sensed by the lead between, on the one hand, the supra-ventricular electrode and one of the first and second atrial electrodes connected to it, and, on the second hand, the other of the first and second atrial electrodes.

2. The single-path lead of claim 1, wherein the electric connection between said one atrial electrode and the supra-ventricular electrode is a connection internal to said lead.

3. The single-path lead of claim 1, wherein the one atrial electrode connected to the supra-ventricular electrode is a proximal electrode and the other atrial electrode is a distal electrode.

* * * * *

UNITED STATES PATENT AND TRADEMARK OFFICE
CERTIFICATE OF CORRECTION

PATENT NO.   : 6,636,770 B2
DATED        : October 21, 2003
INVENTOR(S)  : Alain Ripart It is certified that error appears in the above-identified patent and that said Letters Patent is hereby corrected as shown below:

Column 1,
Line 67, delete "placed indeed" and insert -- placed -- therefor; and

Column 3,
Lines 10-11, delete "electrode proximal 14" and insert -- electrode 14 -- therefor;

Signed and Sealed this

Twenty-sixth Day of July, 2005

JON W. DUDAS
*Director of the United States Patent and Trademark Office*